United States Patent [19]

Grasso et al.

[11] Patent Number: 5,326,865
[45] Date of Patent: Jul. 5, 1994

[54] ARYLAZO AND POLY(ARYLAZO) DYES HAVING AT LEAST ONE CORE RADICAL SELECTED FROM NAPHTHYL OR ANTHRACYL AND HAVING AT LEAST ONE 2,3-DIHYDRO-1,3-DIALKYL PERIMIDINE SUBSTITUENT

[75] Inventors: Robert P. Grasso; Michael K. O'Brien, both of Wilmington, Del.; Paul J. Shannon, Exton, Pa.

[73] Assignee: Hercules Incorporated, Wilmington, Del.

[21] Appl. No.: 535,268

[22] Filed: Jun. 8, 1990

[51] Int. Cl.$^5$ .................... C09B 29/36; C09B 31/14; C09B 31/28; C09K 19/24

[52] U.S. Cl. .................... 534/577; 534/649; 534/653; 534/754; 534/755; 534/757; 534/762; 534/775; 534/778

[58] Field of Search ............... 534/577, 649, 653, 754, 534/755, 757, 762, 775, 778

[56] References Cited

U.S. PATENT DOCUMENTS

| | | | |
|---|---|---|---|
| 4,122,027 | 10/1978 | Cole, Jr. et al. | 534/754 X |
| 4,179,395 | 12/1979 | Cole, Jr. et al. | 252/299 |
| 4,224,071 | 9/1980 | Buell | 534/762 X |
| 4,350,603 | 9/1982 | Aftergut et al. | 252/299.1 |
| 4,565,424 | 1/1986 | Huffman et al. | 534/754 X |
| 4,667,020 | 5/1987 | Etzbach et al. | 534/577 |

FOREIGN PATENT DOCUMENTS

| | | | |
|---|---|---|---|
| 56-99259 | 8/1981 | Japan | 534/762 |
| 62-555 | 1/1987 | Japan | 534/577 |

OTHER PUBLICATIONS

A. F. Pozharskii et al., "π-Donor Characteristics of 1,8-Naphthylenediamines and 2,3-Dihydroperimidines", translated from Zhurnal Organicheskoi Khimil, vol. 16, No. 10, pp. 2216–2228, Oct., 1980.

V. I.-Sokolov et al, "Reaction of 2-Substituted Quaternary Perimidinium Salts with Alkali", translated from Khimiya Geterotsiklicheskikh Soedinenii, No. 6, pp. 849–851, Jun. 1973.

Roger W. Alder et al, "Preparation of a Range of NNN'N'-Tetrasubstituted 1,8-Diaminonaphthalenes", J. Chem. Soc., Pt. 1, 2840 (1981).

Primary Examiner—Mary C. Lee
Assistant Examiner—Fiona T. Powers
Attorney, Agent, or Firm—Mark D. Kuller

[57] ABSTRACT

Arylazo and poly(arylazo) dyes having at least one core radical selected from naphthyl or anthracyl and having at least one 2,3-dihydro-1,3-dialkyl perimidine substituent, a guest-host composition comprising a liquid crystal host solvent and the arylazo or poly(arylazo) dichroic dye, and a liquid crystal display comprising the guest-host composition, are disclosed.

17 Claims, 5 Drawing Sheets

Figure 1

R, R' = alkyl or H
$R_3$-X = $C_1$-$C_{20}$ alkyl halide (iodide or bromide), tosylate or mesylate
$R_3$ = $C_1$-$C_{10}$ alkyl
$R_4$, $R_5$ = H, $C_1$-$C_{20}$ alkyl, or form a cycloaliphatic ring

ARYLAZO AND POLY(ARYLAZO) DYES HAVING AT LEAST ONE CORE RADICAL SELECTED FROM NAPHTHYL OR ANTHRACYL AND HAVING AT LEAST ONE 2,3-DIHYDRO-1,3-DIALKYL PERIMIDINE SUBSTITUENT

This invention is directed to novel arylazo and poly(arylazo) dyes having at least one core radical selected from naphthyl or anthracyl and having at least one 2,3-dihydro-1,3-dialkyl perimidine substituent, a guest-host composition comprising a liquid crystal host solvent and the arylazo or poly(arylazo) dichroic dye, and a liquid crystal display comprising the guest-host composition.

BACKGROUND OF THE INVENTION

The use of dichroic dyes in solution with various liquid crystal materials and use of these so-called "guest-host" mixtures in liquid crystal devices, e.g., liquid crystal displays, are well known. In liquid crystal displays, the host liquid crystal material has its orientation controlled by the application of electric fields which in turn interacts with the guest dichroic dye to induce a cooperative conforming alignment. The dichroic dyes manifest low or high absorbance of incident light depending upon their molecular orientation with respect to the light wave vector. Generally, when an electric field is applied to the display, the area between the electrodes appears clear, i.e., all the dyes exhibit minimum absorption, and in the absence of an electric field the display appears dye colored, i.e., the dyes are in a high absorbing state.

Dyes suitable for such guest-host mixtures must have high order parameters and proper solubility in the host liquid crystal material, and the guest-host mixtures should provide good viewing characteristics (e.g., high contrast), high extinction, and chemical and photochemical stability.

Several patents describe dichroic azo dyes that have N,N'-unsubstituted dihydroperimidines as end group moieties. For example, Huffman et al, in U.S. Pat. No. 4,565,424, describe poly(arylazo) dyes containing a 2,3-dihydro-2,2-disubstituted perimidine moiety; Etzbach et al, in U.S. Pat. No. 4,667,020, describe diazo dyes containing a 2,3-dihydro-2,2-disubstituted perimidine moiety; and Cole, Jr. et al, in U.S. Pat. No. 4,122,027, describe a trisazo dye containing a 2,3-dihydro-2,2-disubstituted perimidine moiety. In each of these cases the nitrogen atoms at the 1 and 3 positions of the dihydroperimidine are bound to a hydrogen atom.

Azo dyes containing dihydroperimidine moieties unsubstituted at the nitrogen positions exhibit relatively low solubility characteristics in nematic hosts. The N-H bonds in the dyes result in relatively high crystalline melting points and thus solubility is reduced. Shannon, in U.S. patent application No. 07/375,166, filed Jul. 3, 1989, discloses that azo dyes having N,N'-disubstituted-2,3-dihydro perimidine end groups, particularly those with alkyl substitution at the 2-position, are more soluble than the same dyes having N—H bonds, and that guest-host mixtures prepared with such dyes have excellent properties, most notably improved contrast.

It is often desired to provide a liquid crystal display which appears neutral black in the absence of an electric field and clear or non-black in the presence of an electric field. Generally, guest-host compositions used in such displays contain at least three dichroic dyes having their absorption maxima centered at approximately 450, 550 and 650 nm (in order to absorb strongly throughout the region between 400 and 700 nm). When using the dyes described by Shannon, supra, in such a formulation it is often necessary to use a dye having a large number of azo groups (i.e., tetra- or penta-azo dyes) to obtain chromophores with absorption at longer wavelengths. These dyes have lower solubilities in host liquid crystals than their shorter chain (fewer azo group) counterparts, making them unsatisfactory for certain guest-host formulations. The inventors have discovered that the wavelength of dye absorption can be shifted toward longer wavelengths by replacing one or more phenyl core radical of the dyes described by Shannon, supra, with a naphthyl or anthracyl radical. The resultant dyes have an appropriate wavelength for preparing black dye formulations and a higher solubility than their longer chain (larger number of azo groups) counterparts.

SUMMARY OF THE INVENTION

Accordingly, this invention is directed to arylazo and poly(arylazo) dichroic dyes having at least one core radical selected from naphthyl or anthracyl and having at least one 2,3-dihydro-1,3-dialkyl perimidine substituent, a guest-host composition comprising a liquid crystal host solvent and the arylazo or poly(arylazo) dichroic dye, and a liquid crystal display comprising the guest-host composition.

DETAILED DESCRIPTION OF THE INVENTION

Preferred are arylazo or poly(arylazo) dichroic dyes having having at least one naphthyl or anthracyl moiety and one 2,3-dihydro-1,3-dialkyl perimidine substituent having the general formula:

wherein A is a naphthyl radical (I), anthracyl radical (II) or anthracyl radical (III) and X is one of the radicals listed for A or a phenyl radical (IV):

(I)   (II)   (III)   (IV)

$R^1$ and $R^2$ are independently $-NO_2$, $-CN$, Br, Cl, F, $-CO_2R^3$, $-NR^4R^5$, $-OR^6$ or $R^6$; $R^3$, $R^4$, $R^5$ and $R^6$ are independently H or $C_1$ to $C_6$ alkyl groups; n and m are integers of 0 through 4; when n=0, Z is selected from the group consisting of $-NO_2$, $-CN$, $-CO_2R^3$, F, Cl, Br $R^6$, $-OR^6$, $-SO_2$, $CH_3SO_2-$, $CF_3SO_2-$, $C_6H_5SO_2-$, $-CF_3$, $-C(O)CF_3$, 2,2-dicyanovinyl and 1,2,2-tricyanovinyl, and wherein $R^7$ is selected from the group consisting of H and $C_1$ to $C_{10}$ alkyl groups; $R^8$ and $R^9$ are independently selected from the group consisting of H and $C_1$ to $C_{20}$ alkyl groups or form a $C_4$ to $C_8$ cycloaliphatic ring; when n is an integer of from 1 through 4, Z is selected from the group described above and $-NR^4R^5$.

B is wherein $R^{10}$ is a $C_1$ to $C_{10}$ alkyl groups, and $R^{11}$ and $R^{12}$ are independently selected from the group consisting of H and $C_1$ to $C_{20}$ alkyl or form a $C_4$ to $C_8$ cycloaliphatic ring.

Preferably $R^{11}$ and $R^{12}$ are selected from H $C_1-C_{20}$ and alkyl.

Preferably, when n=0, Z is selected from $-NO_2$, $-CN$, $-CO$ $R^3$, $CH_3SO_2-SO_2$, $CF_3SO_2-$, $-CF_3$, $-C(O)CF_3$, 2,2-dicyanovinyl and 1,2,2-tricyanovinyl and, when n=an, integer of 1 through 4, Z is selected from any of these and $-NR^4R^5$.

The preferred dyes have one or two perimidines and one napthyl ring.

More preferred are those dyes having n=0 and m=0, n=1 and m=0, or n=1 and m=1; A as the substituent labelled I; and X as the substituent labelled IV. Most preferred are dyes having n=1 and m=0 or 1, A as the substituent labelled I, and X as the substituent labelled IV.

N,N'dialkyl-1,8-naphthalene diamines may be synthesized as disclosed in the literature: A. F. Pozharskii et al, Zh. Org. Khim., 16, (10) 2216 (1980); Chemistry of Heterocyclic Compounds, Plenum Press, New York p 782 (1975) (Translated from Khim. Geterot. Soed., No. 6, 849 (1973)); and R. W. 20 Alder, et al, J. Chem. Soc., Pt. 1, 2840 (1981). They are preferably synthesized according to a new route, first described by Shannon, supra, outlined in FIG. 1. According to the most preferred process, condensation of 1,8-naphthalene diamine with a ketone or aldehyde (e.g., 3-methyl-2-butanone or acetone) gives a 2,3-dihydro-2,2-dialkyl perimidine. This material is alkylated (at room temperature to 80° C.) at each nitrogen atom with an alkyl halide (e.g., bromide or iodide) in a water miscible organic solvent (e.g., acetone and methyl ethyl ketone) and an inorganic base (e.g., potassium carbonate) in a one pot process (optionally, a small amount of water may be used). The steric hindrance about the nitrogen atoms of the 2,3-dihydro-2,2-dialkyl perimidines controls the selectivity of the alkylation reaction. Hydrolysis of the 2,3-dihydro-1,3-dialkyl-2,2-dialkyl perimidine in aqueous acid (e.g., hydrochloric acid) and an aqueous organic solvent (e.g., tetrahydrofuran, methanol, etc., in water) provides N,N'-dialkyl-1,8-naphthalene diamine. Table 1 lists various N,N'-dialkyl-1,8-naphthalene diamines prepared by the route outlined in FIG. 1.

The N,N'-dialkyl-1,8-naphthalene diamines are easily purified by recrystallization. They can then be used to prepare a wide variety of 2-substituted or 2,2-disubstituted 2,3-dihydro-1,3-dialkyl perimidines by condensation with aldehydes or ketones as outlined in FIG. 1. Condensations are usually carried out at room temperature in the presence of a catalytic amount of p-toluene sulfonic acid. An aldehyde or ketone can be used as solvent, as in the case of the acetone adduct, or a slight excess of the aldehyde or ketone can be used in an inert solvent such as tetrahydrofuran or ethyl acetate. Table 2 lists several 2,3-dihydro-1,3-dialkyl perimidines prepared by condensation of aldehydes or ketones with N,N'-dialkyl-1,8-naphthalene diamines.

The poly(arylazo) moieties and their preparation are well-known as shown, e.g., by Huffman et al in U.S. Pat. No. 4,565,424, Jones et al, in U.S. Pat. No. 4,401,369, Cole, Jr. et al, in U.S. Pat. Nos. 4,122,027, 4,128,497 and 4,179,395, Etzbach et al, in U.S. Pat. No. 4,667,020, and Ivashchenko et al, "Dyes in Liquid Crystals", Mol. Cryst. Liq. Cryst., Vol. 150 A, pp. 1–168 (1987).

A preferred synthetic scheme for preparing the dichroic dyes of this invention involves direct diazotization of 1-amino-4-nitro naphthalene in strong mineral acid, followed by coupling of the resultant diazonium compound to the appropriate substituted aniline, perimidine or phenol. Diazotization and coupling can be repeated as desired and the intermediate products recovered from a buffered aqueous solution as the free base and purified by recrystallization. The desired free base can subsequently be diazotized and coupled with a substituted 2,3-dihydro perimidine in acid. The resultant dichroic dye is recovered from the neutralized solution by filtration and is purified by recrystallization or chromatography. Exemplary dyes prepared by these methods are shown in Table 3.

Figure 2:
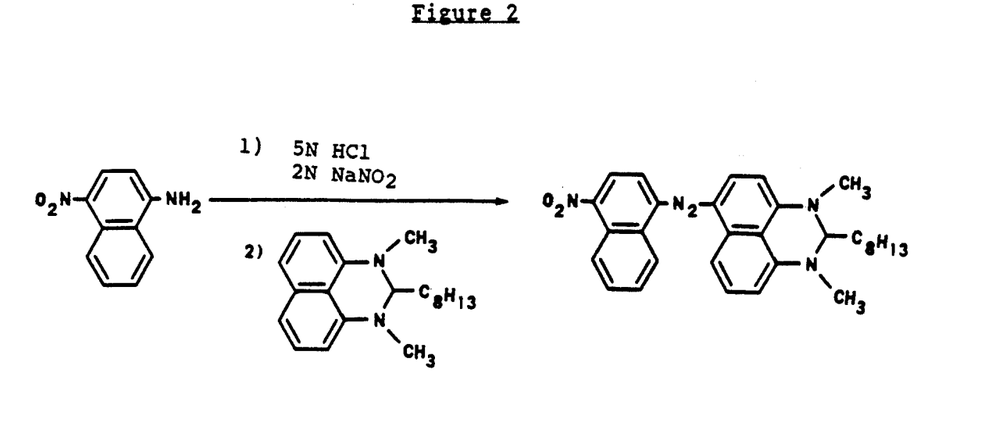
FIG. 2 illustrates a typical monoazo dye which is a useful dye of this invention.

A useful starting material to practice this invention is 1-amino-4-nitro naphthalene. FIG. 2 illustrates a typical synthesis of a monoazo compound which is a useful dye of this invention. Typically, 1-amino-4-nitro naphthalene is dissolved in hydrochloric acid and aqueous sodium nitrite is slowly added at 0° C. to generate the diazonium salt which can then be coupled with 2,3-dihydro-1,3-dimethyl-2-octylperimidine (prepared as described above) to yield the corresponding monoazo nitronaphthyl perimidine.

Figure 3:
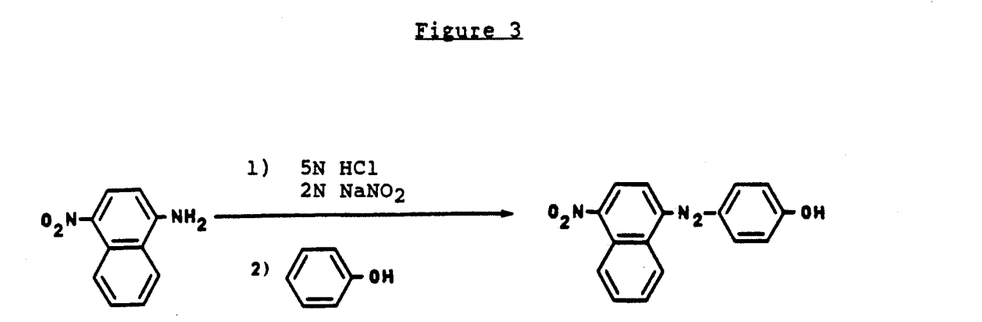
FIG. 3 illustrates the synthesis of monoazo nitronaphtyl phenol which is a useful intermediate in the preparation of the diazo chromophores of this invention.

FIG. 3 illustrates the synthesis of monoazo nitronaphthyl phenol which is a useful intermediate in the preparation of the diazo chromophores of this invention. The diazonium salt of 1-amino-4-nitronaphthalene which is prepared as described above, is coupled to phenol dissolved in glacial acetic acid at 0° C. to produce monoazo nitronaphthyl phenol.

Figure 4:
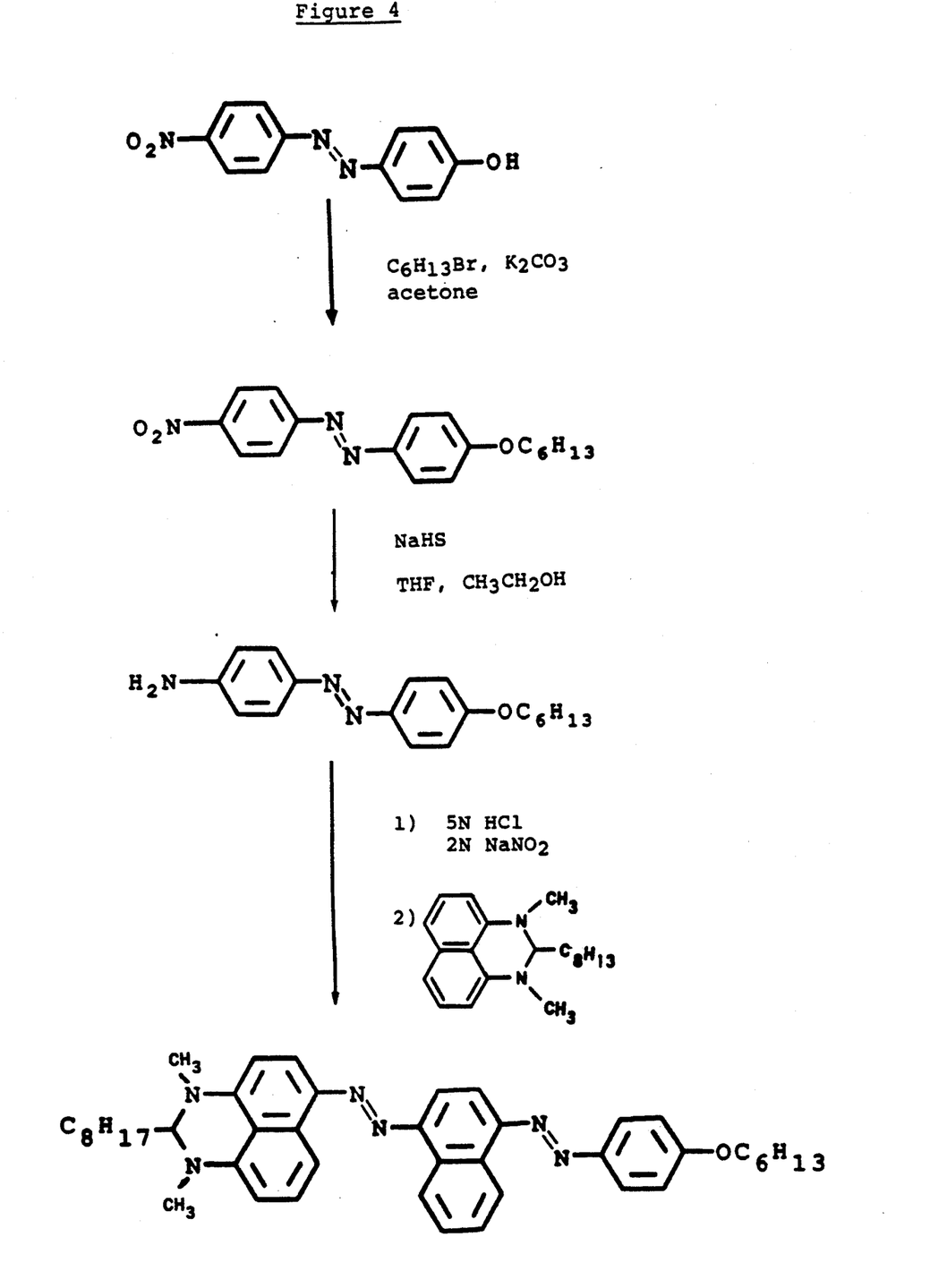
FIG. 4 illustrates the synthesis of a diazo dye from monoazo nitronaphthyl phenol.

Synthesis of a diazo dye from monoazo nitronaphthyl phenol is illustrated in FIG. 4. Monoazo nitronaphthyl phenol is dissolved in an organic solvent (e.g., acetone or 2-butanone) and in succession are added a base (e.g., potassium carbonate) and a $C_1$ to $C_{12}$ alkyl halide. The suspension is refluxed for 6 to 24 hours to yield the corresponding alkoxymonoazonitronaphthyl phenol. After hydrogen sulphide reduction to the corresponding amine, this compound is dissolved in hydrochloric acid and converted to the diazonium salt as described above. Coupling of the diazonium salt with 2,3-dihydro-1,3-dimethyl-2-alkyl perimidine is accomplished at 0° C. in glacial acetic acid to yield the corresponding diazo naphthyl perimidine.

The dichroic dyes of this invention exhibit deep blue color and have absorption maxima in the range of 575 to about 700 nm in $CHCl_3$. They are stable towards UV light and heat.

Although the dyes of this invention may be used in any application where similar dyes may be used, they are primarily intended for use in guest-host liquid crystal mixtures comprising at least one liquid crystal and at least one dichroic dye soluble in the liquid crystal. Herein, the term "liquid crystal" is used to refer to molecules with anisotropic geometry, such as rod-shaped or disc-shaped, that exhibit stable states intermediate between liquid and solid, and which have low molecular weights.

The dyes of this invention are quite soluble in a range of nematic and ferroelectric liquid crystal hosts. The liquid crystal medium of this invention may contain any such liquid crystal compound useful in liquid crystal devices, e.g., liquid crystal displays, or a mixture of such liquid crystal compounds. Useful are thermotropic liquid crystals which exhibit nematic and smectic (including ferroelectric) phases.

Nematic phases include conventional uniaxial nematics, twisted nematic, and cholesteric mesophases. The nematic liquid crystals can have either positive or negative dielectric anisotropy. As used herein the term "positive" or "negative" refers to the net dielectric anisotropy of a mixture comprising liquid crystals.

Readily available positive nematic liquid crystal materials which are suitable for the practice of this invention include: 4-cyano-4'-alkylbiphenyls, 4-cyano-4'-alkyloxybiphenyls, 4-alkyl-(4'-cyanophenyl)cyclohexanes, 4-alkyl-(4'-cyanobiphenyl)cyclohexanes, 4-cyanophenyl-4'-alkylbenzoates, 4-cyanophenyl-4'-alkyloxybenzoates, 4-alkyloxyphenyl-4'cyanobenzoates, 4-alkylphenyl-4'cyanobenzoates, 1-(4'-alkylphenyl)-4-alkylpyrimidines, 1-(4'-alkylphenyl)-4-cyanopyrimidines, 1-(4'-alkyloxyphenyl)-4-cyanopyrimidines and 1-(4-cyanophenyl)-4-alkyl-pyrimidines. Specific examples of compounds within these families are: 4-cyano-4'-pentylbiphenyl, 4-cyano-4'-hexyloxybiphenyl, trans-4-pentyl-(4'-cyanophenyl)-cyclohexane, trans-4-hexyl-(4'-cyanobiphenyl)cyclohexane, 4-cyanophenyl-4'-propylbenzoate, 4-pentyloxyphenyl-4'-cyanobenzoate, 4-hexylphenyl-4'-cyanobenzoate, 1-(4'-pentylphenyl)-4-butylpyrimidine, 1-(4'-butyloxyphenyl)-4-cyanopyrimidine, 1-(4-cyanophenyl)-4-alkylpyrimidine, 4-n-hexylbenzylidene-4'-aminobenzonitrile and 4-cyanobenzylidene-4'-octyloxyaniline. Eutectic mixtures and combinations of all the above are also useful. Illustrative are eutectic mixtures of 4'-alkyl-4-cyanobiphenyls with either 4'-alkyloxy-4-cyanobiphenyls wherein the 4' substituents have 3 to 8 carbons or terphenyl liquid crystals with 4-alkyl or alkyloxy substituents containing 3 to 8 carbon atoms. Representative are the commercially available E7 mixture from BDH, Ltd., Poole, England; ROTN 404, a eutectic mixture of biphenyl pyrimidine liquid crystals from Hoffman La Roche, Nutley, N.J.; PCH 1132, a mixture comprising the 4-alkyl-(4'cyanobiphenyl)cyclohexanes and 4-alkyl-(4'-cyanophenyl)cyclohexanes from EM Industries, Hawthorne, New York; and ZLI 1982, also available from EM Industries.

Representative of nematic liquid crystals having negative dielectric anisotropy that would be useful for this invention include: 4-alkyloxy-4'-alkyloxyazoxybenzenes 4-alkyl-4'-alkyloxyazoxybenzenes, 4-alkyl-4'-acyloxyazoxybenzenes 4-alkyl-4'alkylazoxybenzenes and 4-alkyl-2-cyanophenyl-4'-alkylbiphenyl-1-carboxylates. Specific examples include: p-azoxyanisole, 4-butyl-4'-hexyloxyazoxybenzene, 4-butyl-4'-acetoxyazoxybenzene, 4,4'-bis(hexyl)azoxybenzene, and 4-pentyl-2-cyanophenyl-4'-heptylbiphenyl-1-carboxylate. Commercially available are Licristal S1014 from EM Industries, Hawthorne, N.Y.; and EN-18 from Chisso Corp, Yokohama, Japan.

Smectic A liquid crystals useful in this invention can be of either positive or negative dielectric anisotropy. Smectic A liquid crystals of positive anisotropy include: 4-alkyl-4'-cyanobiphenyls and 4-cyano-4'-alkylbenzylideneanilines, as well as mixtures of 4-alkyl-4"-cyano-p-terphenyls and 4-alkyl-4"-cyanobiphenyls. Also useful are smectic A mixtures derived from electron accepting and electron donating mesogenic cores, for example 4'-alkylphenyl 4-alkylbenzoates and 4'-cyanophenyl-4"-alkyloxybenxoyloxybenzoates. Specific examples of compounds useful as smectic A liquid crystals with positive dielectric anisotropy are: 4-cyano-4'-octylbenzylideneaniline, 4-decyl-4'-cyanobiphenyl, 4-dodecyl-4"-cyano-p-terphenyl, 4'-heptylphenyl-4-butylbenzoate and 4'-cyanophenyl-4"-octyloxybenzoyloxybenzoate. Eutectic mixtures and combinations of all the above smectic A materials are useful. Representative eutectic mixtures and combinations of smectic A liquid crystals are the commercially available materials S1, S2, S3, S4, S5, S6 and S7, from EM Industries, Hawthorne, N.Y.

Representatives of smectic A liquid crystals of negative dielectric anisotropy that are useful in this invention are 4-alkylphenyl-4-alkyloxy-3-cyanobenzoates, 4-alkyloxyphenyl-4-alkyloxy-3-cyanobenzoates and 4"-alkyloxyphenyl-4'-alkyloxybenzoyloxy-3-cyanobenzoates. Specific examples include: 4'-octylphenyl-4-decyloxy-3-cyanobenzoate, 4'-decyloxyphenyl-4-octyloxy-3-cyanobenzoate and 4'-heptyloxyphenyl-4'-decyloxybenzoyl-3-cyanobenzoate. Eutectic mixtures of these may also be used.

Representative chiral smectic C liquid crystals useful in the practice of this invention include: 4'-alkyloxyphenyl-4-alkyloxybenzoates, 4'-alkyloxybiphenyl-4-alkyloxybenzoates, and 4-alkyloxyphenyl-4-alkyloxybiphenylcarboxylates. Specific examples are: 4(4-methylhexyloxy)phenyl-4-decyloxybenzoate, 4-heptyloxyphenyl-4(4-methylhexyloxy)benzoate, 4'-octyloxybiphenyl-4(2-methylbutyloxy)benzoate, and 4-nonyloxyphenyl-4'-(2-methylbutyloxy)biphenyl-4-carboxylate. Commercially available mixtures of chiral smectic C liquid crystals include the CS 1000 and CS 2000 series offered by Chisso Corp., Yokohama, Japan; the ZLI series, such as ZLI 3654 and ZLI 4139, available from EM Industries, Hawthorne, N.Y.; and the eutectic mixtures of laterally fluorinated esters developed by BDH, LTD., and available through EM Industries as the SCE series of eutectic mixtures SCE3 through SCE12. Single component chiral smectic C materials based on 4'-alkyloxyphenyl-4-alkyloxybenzoates, W7, W37, W81, and W82 are available from Displaytech, Inc., Boulder, Colo.

The substituents on the dye can be varied to alter their solubility. For example, solubility in host liquid crystals increases with increasing length of an alkyl chain at the number two position of the 2,3-dihydro-1,3-dialkyl perimidine substituent, when the alkyl chain has 1 to 8 carbon atoms. The solubility then decreases with homologs greater than $C_8$.

In guest-host mixtures, the dyes of this invention may be used in combination with other dyes. Dyes useful in these mixtures include dichroic azo, bisazo, trisazo, tetrakisazo, pentakisazo, anthraquinone, mericyanine, methine, 2-phenylazothiazole, 2-phenylazobenzthiazole, 4,4'-bis(arylazo)stilbenes, perlyne and 4,8-diamino-1,5-naphtaquinone dyes, and other dyes that exhibit dichroic absorption bands. When a liquid crystal display which appears neutral black in the absence of an electric field and clear or non-black in the presence of an electric field is desired, it is common to use at least three dichroic dyes having their absorption maxima centered at approximately 450, 550 and 650 nm (in order to absorb strongly throughout the region between 400 and 700 nm).

One major advantage of the dyes of this invention is their absorption of higher wavelengths than comparable dyes having all phenyl azo groups. That is, a mono- or bis-azo dye according to this invention may have similar absorption to a similar tris-, tetrakis- or pentakis-azo dye prepared with repeating units such as (IV) above. This result is especially significant when smectic, such as smectic A, C, H or I, or other liquid crystals requiring dyes with high solubilities are used. The shorter chain dyes (having lower number of azo groups) are found to be more soluble than their longer chain (having a higher number of azo groups) counterparts in smectic, most notably smectic C, liquid crystals. To this extent, the shorter chain (lower number of azo groups, such as mono-, his- and tris-azo) dyes are the preferred dyes of this invention, with mono- and bis-azo dyes being most preferred. (This statement should not be taken to diminish the importance of the ability to produce tetra- and penta-azo dyes having higher wavelength absorption for applications where the properties of such dyes are desired).

The dyes of this invention exhibit relatively high order parameter and contrast in liquid crystal hosts.

The dyes of this invention have relatively high extinction coefficients. The molar extinction coefficient is a measurement of the extent to which the dye absorbs light at any particular molar concentration. Higher molar extinction coefficients translate into display systems which exhibit higher contrast ratios at a given molar concentration.

Guest-host systems made with the dyes of this invention are useful in liquid crystal display devices having conventional configurations (e.g., two, three or more substrate structures) and may include one or more polarizers, lighting means, reflective or transflective layers, alignment layers, elastomeric connectors and circuit boards as conventionally used in the art. Other conventional materials such as conducting ionic dopants, chiral dopants, photostabilizers and viscosity modifiers, etc., may be used.

Arylazo and poly(arylazo) dichroic dyes of this invention are particularly useful in the formation of black dye mixtures. Their relatively high solubility allows for high dye concentrations in the neutral black mixtures which, as a result, exhibit high contrast. Dyes of this invention are especially useful for preparing chiral smectic C guest-host systems, particularly those useful in display devices.

Figure 5:
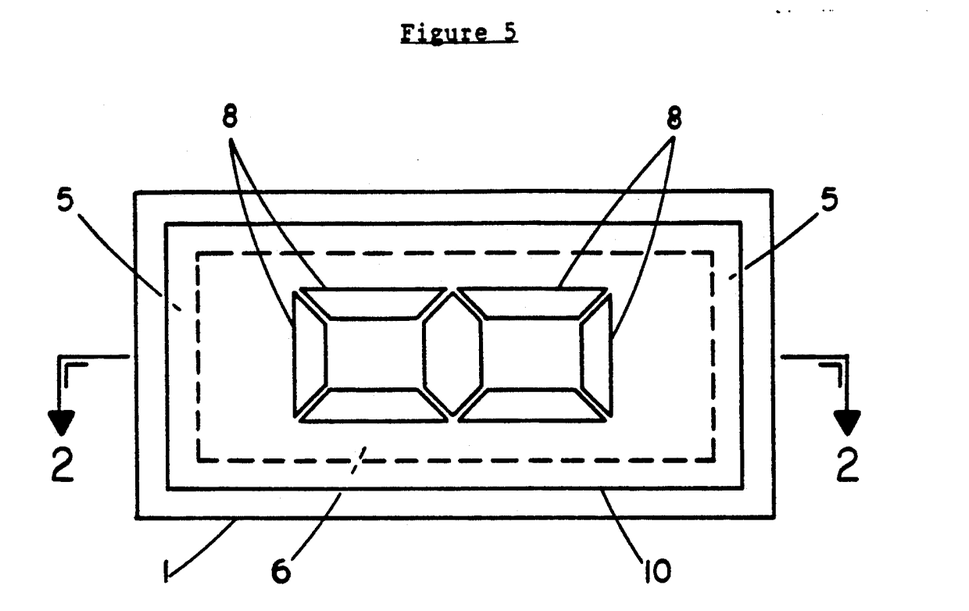
FIG. 5 shows an electronic liquid crystal display suitable for the guest-host mixture of this invention.
Figure 6:
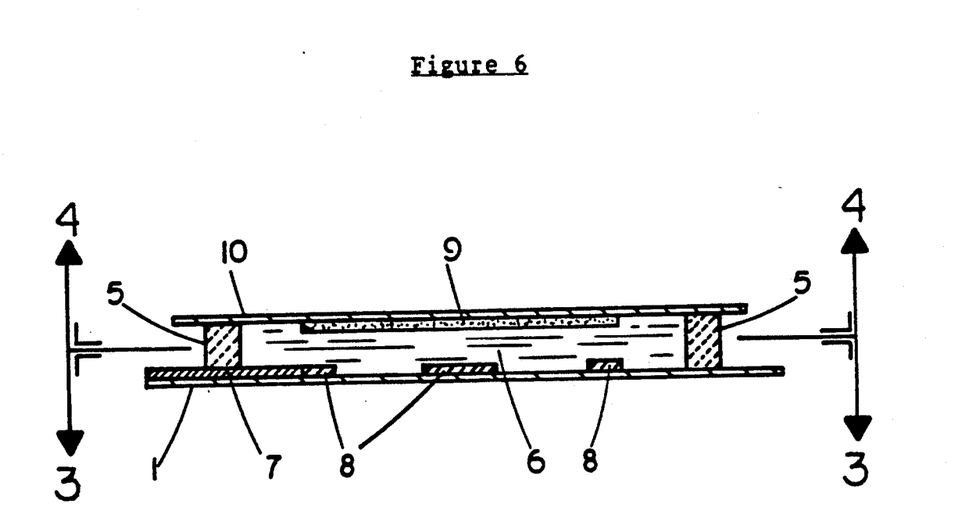
FIG. 6 shows a cross sectional view of an electronic liquid crystal display suitable for the guest-host mixture of this invention.

The guest-host composition is typically placed in a cell comprising two glass substrates coated with transparent electrodes and other compositions (e.g. alignment layer(s)), spacer material(s) and having an adhesive layer perimeter as shown in FIGS. 5 and 6. The liquid crystal and dye molecules of the guest-host composition are generally aligned predominantly parallel to the glass substrates with the smectic layers of the liquid crystal arranged perpendicular to the glass substrates. Upon application of an alternating electric field, the orientation of the host molecules will change with the direction of the electric field. The guest dye molecules will orient along with those of the host and result in a significant change in the intensity of the absorption of the dye(s). The magnitude of the absorption depends upon the molecular orientation with respect to the direction of the polarizer.

Figure 7:
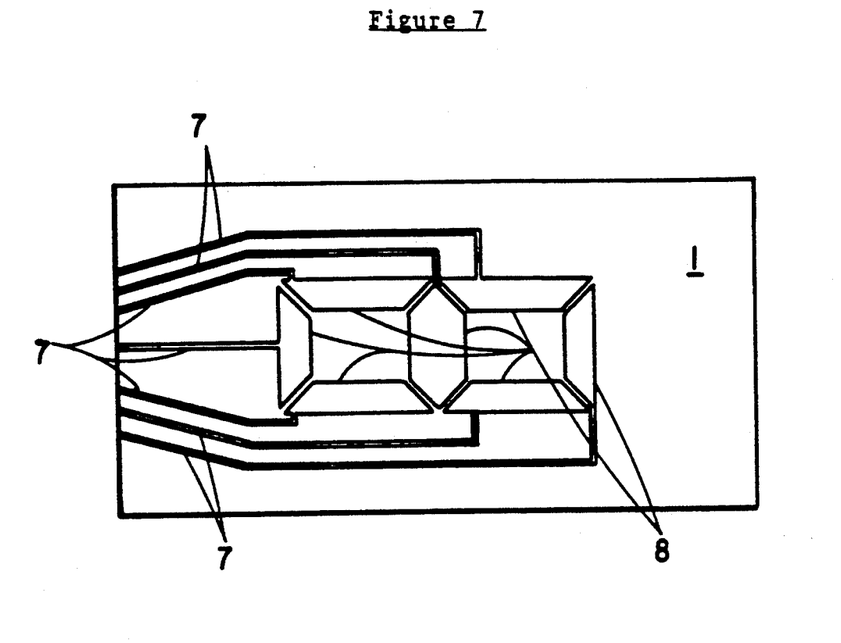
FIG. 7 shows the substrate with electrical leads and symbol-forming patterns of an electronic liquid crystal display.

An electronic liquid crystal display suitable for the guest-host mixture of this invention is shown in FIGS. 5 through 7. The display is depicted as having two substrates, 1 and 10, such as glass, at least one of which must be transparent so as to permit passage of light.

Substrates 1 and 10 are joined together at their perimeters by adhesive layer 5 thereby forming a thin cell 6 which is filled with the guest-host mixture. That is, selected dyes are mixed in the liquid crystal host, usually at elevated temperatures. The solutions are filtered to remove insolubles and the solutions are allowed to fill the display cells by capillary action.

The interior side of each substrate is selectively coated with transparent electrical conductive material, e.g., tin oxide or, preferably, indium tin oxide, so that an electric signal may be applied to the interior of the display device. In FIGS. 5, 6 and 7, the electrically conductive material on substrate 1 is shown as two components, i.e., electrical leads 7 and symbol-forming patterns 8. Electrical leads 7 provide a means for applying an electrical signal to the figure-forming patterns 8 and 9. Figure-forming patterns 8 form one electrode which, along with electrically conductive-coating 9 on substrate 10, form two electrodes which allow a voltage to be applied across the thin layer of the guest-host material 6 to turn on the individual pixels. At least one polarizer 11 is required to provide the desired contrast. Not shown are alignment layers, which are generally thin polymer coatings comprising polyamides, polyimides or other such materials.

Liquid crystal displays of this type are often used in modules containing lighting means (e.g., incandescent or electroluminescent lights), electronic chips and reflectors or transflectors. The reflectors and transflectors may be adhered to a substrate of the display.

Such guest-host systems are useful for other liquid crystal devices, e.g., all-optical light modulators, erasable read/write optical data storage media, etc. Depending on the choice of liquid crystal host, very fast (less than 100 microseconds response time) bistable displays are also attainable.

Since arylazo chromophores often exhibit high degrees of optical non-linearity (both 2nd and 3rd order), the dyes of the invention may be useful components of non-linear optical devices such as electro optical wave guides, second harmonic generators, frequency doublers and all optical logic gates (NOR, XOR, NAND gates, etc.). The dyes are also useful in textiles, printing, color filters, polarizers, paints, etc.

This invention is demonstrated in the following examples, which are illustrative and not intended to be limiting, wherein all percentages, are by weight.

The liquid crystal materials used in the examples are SCE10 (BDH Limited) and ZLI 3654 (EM Industries) which are smectic C ferroelectric mixtures. All of the other starting materials were purchased from Aldrich Chemical Co., Inc., Milwaukee, Wis., or Alfa Products, Ward Hill, Mass., and were used without purification unless otherwise indicated.

EXAMPLE 1

Figure 1:
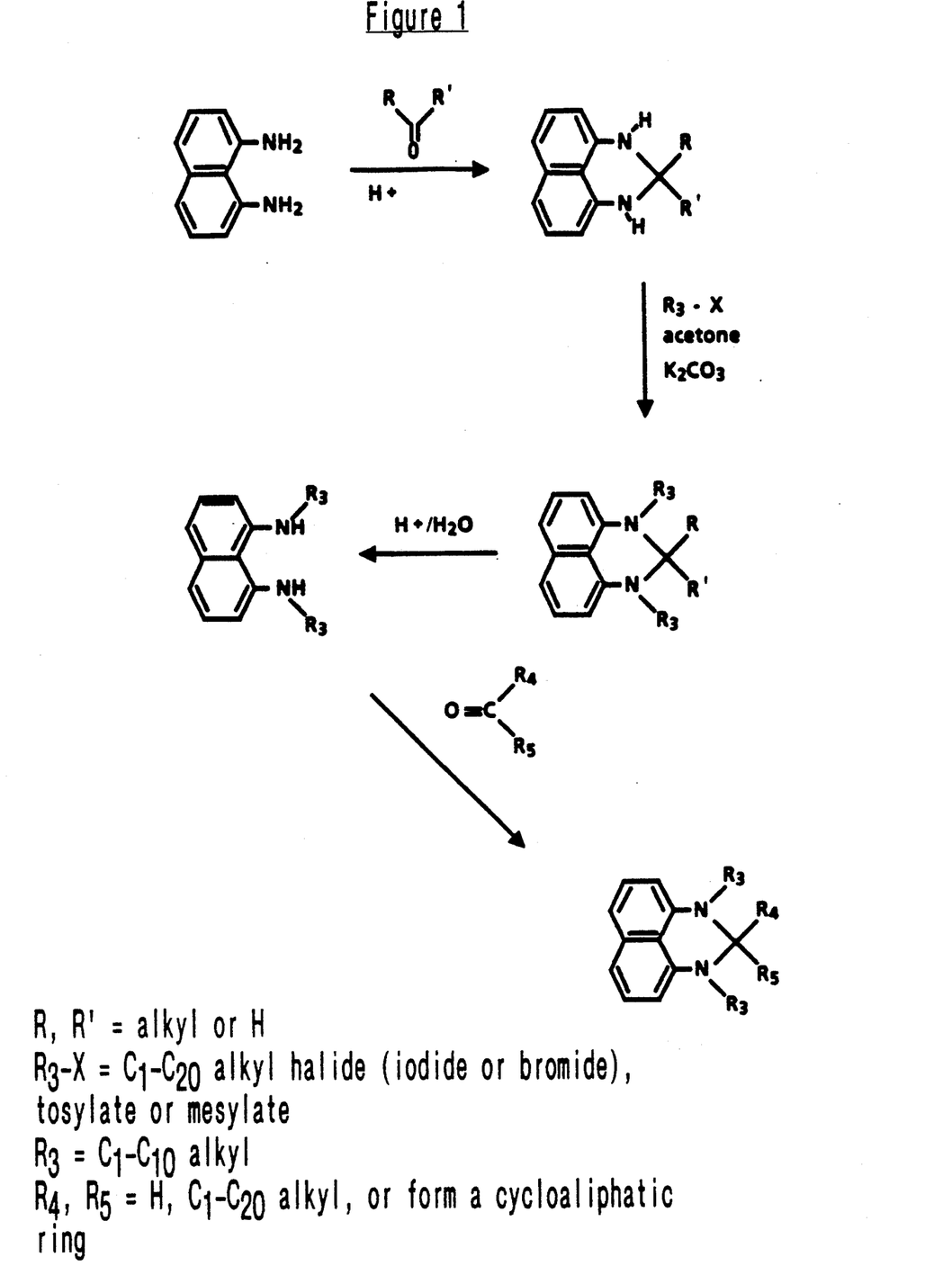
FIG. 1 outlines the condensation reaction of N,N'-dialkyl-1,8-naphthalene with aldehydes or ketones to prepare 2-substituted or 2,2-disubstituted 2,3-dihydro-1,3-dialkyl perimidines.

This example illustrates the preparation of a N,N'-dimethyl-1,8-naphthalene diamine shown in Table 1 using the procedure of FIG. 1.

1,8-Naphthalene diamine (Aldrich Chemical Co.) was distilled on a Kugelrohr distillation apparatus at 140°–160° C. (0.1 mm Hg) to give a pink solid. Then, a mixture of the distilled 1,8-naphthalene diamine (21.8 g, 0.138 mol), p-toluene sulfonic acid (0.75 g), and 3-methyl-2-butanone (24.6 g, 0.30 mol) was prepared, stirred at 50°–60° C. for 1 hour, and allowed to sit overnight at room temperature. The mixture was transferred to a 500 ml 3-neck flask. Water (30 ml), acetone (150 ml), potassium carbonate (84 g, 0.6 mol), and iodomethane (84 g, 0.60 mol) were added and the mixture mechanically stirred at 60°–70° C. for 2 hours, after which more iodomethane (21.0 g, 0.15 mol) was added. The reaction was monitored by thin layer chromatography (TLC) using hexane-ethyl acetate (5:1) as an eluting solvent. After 5.5 hours, the excess methyl iodide and some acetone (25 ml) was distilled and the mixture diluted with water (500 ml) and extracted with ether (2 times, 400 ml and 200 ml portions). The ether extracts were washed with brine and concentrated to a black solid. The solid was dissolved in tetrahydrofuran (THF) (100 ml) and 2N HCl (300 ml). The THF and 100 ml of the water was distilled. TLC indicated that the hydrolysis reaction was complete. The mixture was cooled, basified to a pH greater than 11 with ammonium hydroxide (150 ml) and extracted with ether (400 ml and 200 ml portions). The extract was washed with brine, dried over potassium carbonate and concentrated to a solid. The solid was distilled (Kugelrohr, 98°–102° C., at 0.1 mm Hg) to give a beige solid (21.4 g). The solid was dissolved in hot ethyl acetate (40 ml) and diluted with hexane (160 ml). Cooling gave crystals of N,N'-dimethyl-1,8-naphthalene diamine (15.1 g, 59%): melting point (mp) 102°–104° C.; NMR (CDCl$_3$) 7.15(m, 4H), 7.5(d of d, 2H), 5.4(bs, 2H), 2.85(s, 6H); IR (KBr) 3360, 1595 cm$^{-1}$.

EXAMPLE 2

This example illustrates the synthesis of a N,N'-dibutyl-1,8-naphthalene diamine shown in Table 1 using the procedure of FIG. 1.

A mixture of distilled 1,8-naphthalene diamine (0.14 mol) (distilled as described in Example 1), 3-methyl-2-butanone (24.6 g, 0.28 mol) and p-toluene sulfonic acid (0.75 g) was prepared and stirred at room temperature for 1 hour, and, then, allowed to sit overnight. Acetone (150 ml), water (30 ml), potassium carbonate (84 g, 0.61 mol), and n-butyl iodide (110 g, 0.60 mol) were added to the mixture, the mixture was heated to 60°–70° C., and stirred at that temperature for 25 hours. Potassium carbonate (42.0 g, 0.305 mol) and n-butyl iodide (55 g, 0.30 mol) were added, the mixture was heated to 60°–70° C., and stirred at that temperature for 19 hours. The mixture was diluted with water (750 ml) and extracted with ether (600 ml and 300 ml portions). The extract was washed with brine, dried over potassium carbonate, and concentrated. The mixture was heated in a Kugelrohr apparatus to 60° C. at 0.1 nun Hg to remove 1-butanol. The remaining mixture, comprising the dialkylated, monoalkylated and nonalkylated product (by TLC analysis) was purified by column chromatography on silica (hexane-ethyl acetate, 20:1) to give predominately the desired dialkylated product (20.7 g). The material was dissolved in THF (100 ml) and 2N HCl (300 ml) and heated to distill THF (100 ml). The mixture was basified with ammonium hydroxide, and extracted with ether (400 ml and 200 ml portions). The extract was washed with brine, dried over potassium carbonate, and concentrated. The residue was distilled on a Kugelrohr apparatus up to 120° C. (0.1 mm Hg) to give a beige solid (12.8 g). Recrystallization from ethyl acetate-hexane (3:2) gave N,N'-dibutyl-1,8-naphthalene diamine as needles (5.4 g, 14%): mp 63°–64° C.; NMR (CDCl$_3$) 7.1(m 4H) 6.4(m 2H) 5.35(bs 2H) 3.02(t 4H) 18–1.3(m, 8H), 0.95(t, 6H),; IR (KBr) 3330, 1595 cm$^{-1}$.

EXAMPLE 3

This example illustrates the preparation of a N,N'-dioctyl-1,8-naphthalene diamine shown in Table 1 using the procedure of FIG. 1.

A mixture of distilled 1,8-naphthalene diamine (15.8 g, 0.10 mol) (distilled as described in Example 1), acetone (100 ml) and p-toluene sulfonic acid (0.50 g) was prepared and stirred at room temperature for 15 minutes. Potassium carbonate (55.0 g, 0.40 mol), water (20 ml) and n-octyl iodide (96 g, 0.40 mol) were added to the mixture, and the mixture heated to 65°–70° C. and stirred for 24 hours. Potassium carbonate (27.5 g, 0.20 mol) and n-octyl iodide (48 g, 0.20 mol) were added and the heating continued for another 24 hours. The mixture was diluted with water and extracted two times with 500 ml portions of ether. The ether extract was washed with water and brine, dried over potassium carbonate, and concentrated. The mixture was heated in a Kugelrohr apparatus to 80° C. at 0.1 mm Hg to remove excess n-octyl iodide. The remaining material in the pot was purified by chromatography to give 14.5 g of an oil. The oil was dissolved in THF (200 ml) and 2N hydrochloric acid (200 ml) and heated to distill all the THF and 100 ml of the aqueous acid. The mixture was basified with ammonium hydroxide, and extracted with ether (500 ml and 300 ml portions). The extract was washed with brine, dried over potassium, and concentrated. The residue was purified by chromatography with hexane-ether 20:1 to give a tinted orange solid (2.0 g): mp 42°–43° C.; NMR (CDCl₃) 7.1 (m, 4H), 6.45(m, 2H), 5.42(bs, 2H), 3.05(t, 4H), 1.8–1.3(m, 24H), 0.95(t, 6H); IR (CHCl₃) 3330, 1598 cm⁻¹.

TABLE 1

N,N'-Dialkyl-1,8-Naphthalene Diamines of Examples 1-3

| Example No. | R₃ | Melting Point (°C.) |
|---|---|---|
| 1 | CH₃ | 101.5–103.5 |
| 2 | C₄H₉ | 63–64 |
| 3 | C₈H₁₇ | 42–43 |

EXAMPLE 4

This example illustrates the preparation of 2,3-dihydro-1,3-dimethyl-2-octyl perimidine (shown in Table 2), an intermediate used for preparing dichroic dyes per the instant invention.

A mixture of N,N'-dimethyl-1,8-naphthalene diamine (prepared in Example 1)(5.0 g, 27 mmol), nonyl aldehyde (3.23 g, 30 mmol), p-toluene sulfonic acid (50 mg), and tetrahydrofuran (50 ml) was stirred at room temperature for minutes. The mixture was basified with 25% sodium hydroxide (1.0 ml), diluted with water (100 ml) and extracted with ether (300 ml). The extract was dried over potassium carbonate, concentrated to an oil and recrystallized from hexane ether (10:1) to give 2,3-dihydro-1,3-dimethyl-2-octyl perimidine: mp 62°–63° C.; NMR (CDCl₃) 7.1(m, 4H), 6.3(m, 2H), 4.25(t, 1H), 3.02(s, 6H), 1.6–1.10(m, 14H), 0.85(t, 3H); IR (KBr) 1598 cm⁻¹.

EXAMPLE 5

This example illustrates the preparation of 2,3-dihydro-1,3-dimethyl-2-dodecyl perimidine (shown in Table 2), an intermediate used for preparing dichroic dyes per the instant invention.

A mixture of N,N'-dimethyl-1,8-naphthalene diamine (prepared in Example 1)(0.50 g, 2.7 mmol, 186), tridecanal (0.56 g, 2.85 mmol. 197), p-toluenesulfonic acid (5 mg), and tetrahydrofuran (5 ml) was stirred at room temperature for 15 minutes. The mixture was basified with 25% sodium hydroxide (1.0 ml), diluted with water (20 ml) and extracted with ether (100 ml). The extract was dried over potassium carbonate, concentrated to give 2,3-dihydro-1,3-dimethyl-2-dodecyl perimidine as a solid: mp 30°–32° C.; NMR (CDCl₃) 7.13(m, 4H), 6.32(d, 2H), 4.27(t, 1H), 3.02(s, 6H), 1.7–1.1(m, 22H), 0.85(t, 3H); IR (neat) 1595 cm¹.

TABLE 2

2,3-Dihydro-1,3-Dialkyl Perimidines

| Example No. | R₃ | R₄ | R₅ | Melting Point (°C.) |
|---|---|---|---|---|
| 4 | CH₃ | H | C₈H₁₇ | 62–63 |
| 5 | CH₃ | H | C₁₂H₂₅ | 30–32 |

EXAMPLE 6

This example illustrates the formation of the monoazo nitronaphthyl perimidine 6 (shown in Table 3) via an azo coupling reaction between 1-amino-4-nitronaphthalene and 2,3-dihydro-1,3-dimethyl-2-octyl perimidine.

2 ml of 5N HCl, and 1-amino-4-nitronaphthalene (Aldrich Chemical Co.) (357 mg, 1.9 mmol) were stirred in a beaker at room temperature for 15 minutes. Small aggregates were broken up with a glass stirring rod so that the yellow suspension was relatively uniform. After cooling to 0° C. in an ice bath, 1.2 ml of 2N NaNO₂ was added in 3 portions over 15 minutes. After 45 minutes, the suspension was allowed to warm to room temperature and an additional 2 ml of 5N HCl was added. Every 30 minutes, 100 to 150 microliters of 2N NaNO₂ was added until a total of 1 ml had been added. The color of the suspension turned progressively orange/red over the course of the reaction. After 6 hours, the suspension was again cooled to 0° C. and its contents were added to a second beaker which contained 2,3-dihydro-1,3-dimethyl-2-octyl perimidine (prepared according to the procedure of Example 4) (660 mg, 1.9 mmol), glacial acetic acid (3.8 ml) and sodium acetate (570 mg, 6.95 mmol) at 0° C. After 20 minutes, the viscous blue/black mixture was basified with saturated Na₂CO₃ (pH=6–7) and the resulting blue/black crystals were filtered and dried on the vacuum line overnight. Flash chromatography on silica gel (30:70 THF/Hexane as eluant) followed by recrystallization from ethanol/THF (10:1) yielded 330 mg (34%) of pure blue crystals. Melting point ("mp")=105°–107° C. 1H NMR (CDCl₃) delta=8.5–6.5 (11H, m); 3.2 (3H, s, NMe); 3.08 (3H, s, NMe); 2.5–1.5 (17H, m). Lambda max (CH₂Cl₂)=600 nm; e=26,520.

EXAMPLE 7

This example illustrates the preparation of the diazo perimidine dye 7 shown in Table 3.

The monoazo nitro naphthyl phenol was prepared as follows: 1-amino-4-nitronaphthalene (10.0 g, 53.2 mmol), 5N HCl (63 ml, 315 mmol) and 42 ml of distilled water were stirred with a spatula in a 200 ml beaker. After cooling the yellow suspension to 0° C., 2M NaNO$_2$ (28.9 ml, 57.8 mmol) was added dropwise over 30 minutes. The suspension was stirred an additional 30 minutes at this temperature and stirring for 6 hours. The mixture was again cooled to 0° C. and the contents were added to a second beaker containing phenol (5.9 g, 62.7 mmol), glacial acetic acid (126 ml) and sodium acetate (16.8 g) at 0° C. The orange/red suspension was stirred at 0° C. for 1 hour before the contents were slowly basified to a pH of 7 with saturated Na$_2$CO$_3$. The red solid was filtered and washed with liberal amounts of water. Flash chromatography (40:60 THF/hexane as eluant) yielded 10.2 g (65%) monoazo nitronaphthyl phenol as an orange solid. mp=180° C. 1H NMR (CDCl$_3$) delta 9.0–6.8 (10H, m) IR (CHCl$_3$) v$_{max}$ 3370, 1608, 1600, 1515 cm$^1$.

The monoazo nitronaphthyl phenol prepared above (3.5 g, 11.93 mmol) was dissolved in 42 ml of reagent grade acetone in a 3-neck round-bottomed flask fitted with a reflux condenser and stirred under nitrogen. Potassium carbonate (3.36 g, 17.0 mmol) and 1-bromohexane (2.02 ml, 10.2 mmol) were successively added and the resulting blue suspension was refluxed for 16 hours. The reaction was cooled, extracted with ether, washed with water, 2N HCl, water and saturated sodium bicarbonate, dried over MgSO$_4$, filtered and concentrated in vacuo to yield 4.4 g (98%) of hexyloxy monoazo nitronaphthyl phenol as an orange/red solid, which was used directly in the next step. mp=68°–70° C. 1H NMR (CDCl$_3$) delta=8.8–6.6 (10H, m); 3.85 (2H, t); 2.0–0.5 (11H, m). IR (CHCl$_3$) v$_{max}$ 1600 1582 1520 1298 cm$^{-1}$.

The hexyloxy monoazo nitronaphthyl phenol prepared above (4.4 g, 11.67 mmol) was dissolved in a solution of THF (77 ml) and absolute ethanol (150 ml) and heated with stirring under nitrogen to about 65° to 70° C. Sodium hydrogen sulfide (6.17 g, 110 mmol) dissolved in 22 ml of distilled water was added at this temperature in one portion. After stirring 5 hours the solution was poured into 200 ml of distilled water and the resulting red crystals were filtered and dried on a vacuum line overnight (3.81 g, 94% yield). Recrystallization from THF:ethanol yielded 3.2 g of hexyloxy monoazo naphthyl amine as red crystals. $^1$H NMR (CDCl$_3$) delta 8.9 (1H, d); 8.0–6.7 (9H, m); 4.45 (2H, br s); 3.9 (2H, t); 2.0–0.6 (11H, m).

To the hexyloxy monoazo naphthyl amine prepared above (300 mg, 0.86 mmol) in a small beaker was added 5N HCl (2 ml, 10 mmol) with stirring at room temperature. After cooling to 0° C., 2N NaNO$_2$ (0.5 ml, 0.95 mmol) was added in 3 portions over 15 minutes. After stirring at this temperature for 30 minutes, the mixture was added to a second beaker which contained 2,3-dihydro-1,3-dimethyl-2-hexyl perimidine (prepared in the same manner as described for the 1,3-dimethyl-2-octyl perimidine in Example 4 except that heptanal is used in place of nonyl aldehyde) (270 mg, 1.03 mmol), glacial acetic acid (2.9 ml) and sodium acetate (366 mg, 4.47 mmol) at 0° C. After 30 minutes, the blue/black suspension was basified (pH=7.0) with saturated sodium carbonate and filtered to yield 520 mg of a blue/black solid. Flash chromatography (15:85 THF/hexane as eluant) followed by recrystallization from THF:hexane (1:10) yielded 120 mg of pure diazo naphthyl perimidine 28736-41. mp=62°–67° C. 1H NMR (CDCl$_3$) delta=9.2–6.2 (15H, m); 4.4 (1H, m) 4.0 (2H, t); 3.2 (3H, s), 3.0 (3H, s); 2.0–0.6 (24H, m). IR (CHl$_3$) v$_{max}$ 1590 cm$^1$.

EXAMPLE 8

The following example illustrates the preparation of the diazo perimidine dye 8 shown in Table 3.

To the hexyloxy monoazo naphthyl amine, prepared as described in the previous example (800 mg, 2.32 mmol), in a small beaker at room temperature was added 3 ml of 5N HCl and 2 ml of distilled water. The blue/black suspension was cooled to 0° C. and 2M NaNO$_2$ (1.3 ml, 2.52 mmol) was added in 3 portions over 15 minutes. This suspension was warmed to room temperature, stirred for 1 hour, cooled back to 0° C. and added to a second beaker which contained 2,3-dihydro-1,3-dimethyl-2-octyl perimidine (prepared according to the procedures of Example 4) (836 mg, 2.78 mmol), glacial acetic acid (6 ml) and sodium acetate (984 mg) at 0° C. The resulting slurry was stirred for 30 minutes at this temperature before basifying with saturated sodium carbonate (pH=7) and filtering the blue/violet crystals. Flash chromatography (15:85 THF/hexane as eluant) followed by recrystallization (THF:ethanol, 1:10) yielded 520 mg of pure diazo perimidine 8 (40%). mp=122°–125° C. 1H NMR (CDCl$_3$) delta 9.1–6.5 (15H, m,); 4.3 (1H, t); 3.96 (2H, t); 3.1 (3H, s); 2.95 (3H, s); 1.9–0.6 (26H, m). IR (CH$_2$Cl$_2$) v$_{max}$ 1588 cm$^1$. Lambda max (CHCl$_3$) 585 nm. e (e=epsilon)=32,215. Solubility in ZLI 2454 (nematic)=4.119 wt %. Solubility in SCE11=3.0 wt %. Solubility in ZLI 3654=2.5 wt %.

EXAMPLE 9

This example illustrates the preparation of diazo perimidine dye 9 shown in Table 3.

Dodecyloxy monoazo naphthyl amine was synthesized as described above for the hexyloxy monoazo naphthyl amine (C$_{12}$H$_{25}$Br used instead of C$_6$H$_{13}$Br). To this amine (1.8 g, 4.18 mmol) in a small beaker was added 5N HCl (5 ml, 25 mmol) and 6 ml of water at room temperature with stirring. After cooling to 0° C., 2N NaNO$_2$ (2.3 ml, 4.6 mmol) was added in three portions over 30 minutes. The blue/black suspension was warmed to room temperature, stirred for 30 minutes, again cooled to 0° C. and added to a second beaker containing 2,3-dihydro-1,3-dimethyl-2-dodecyl perimidine (prepared as described in Example 5)(1.8 g), glacial acetic acid (10.5 ml) and sodium acetate (1.8 g) at 0° C. After stirring at this temperature for an additional 30 minutes, the suspension was basified (pH=7) with saturated sodium carbonate and filtered to give a dark blue solid. Flash chromatography (15:85 THF/hexane as eluant) followed by recrystallization (THF:ethanol, 1:10) yielded 700 mg of the diazo dodecyloxy naphthyl perimidine as blue crystals. mp=98°–99° C. 1H NMR (CDCl$_3$) delta 9.2–6.5 (15H, m); 4.4 (1H, t); 4.1 (2H, t); 3.2 (3H, s); 3.1 (3H, s); 1.8–0.6 (48H, m). IR (CHCl$_3$) V$_{max}$ 1600, 1590 cm$^1$. Lambda max=589 nm (CHCl$_3$), e=27,447. Solubility in ZLI 2452 was 2.088 wt. %. Solubility in SCE11 was 2 wt %.

TABLE 3

Example No.

6.

7.

8.

9.

EXAMPLE 10

This example illustrates the formation of a bisazohexyloxyphenol, a yellow dye.

Monoazo amine was prepared as follows. To a suspension of 4-hexyloxyaniline (5.8 g, 30 mmol, 193) in 10N hydrochloric acid (10 ml) and water (30 ml) was added 2M sodium nitrite solution (16 ml, 32 mmol) over 5 minutes at 0°–5° C. The solution was stirred occasionally over 30 minutes at 0°–5° C. In a second beaker 2-methoxy-5-methyl aniline (5.5 g, 40 mmol),' sodium acetate (8.4 g, 0.1 mol) and acetic acid (50 ml) were mixed well for 5 minutes and cooled to 0°–5° C. The diazonium solution was added to the acetic acid solution all at once and the mixture stirred over 30 minutes at 0°–5° C. The mixture was basified with 25% sodium hydroxide to a pH of 10, filtered, and the solid was washed with hot water. The solid was dried under vacuum and recrystallized from ethanol to give monoazo amine (6.36 g, 62%): mp 97° C.; NMR (CDCl$_3$) 7.7 and 6.85(2d, 4H), 7.2 and 6.47(2s, 2H), 4.0(m, 4H), 3.8(s, 3H), 2.57(s, 3H), 1.9–1.2(m,8H), 0.9(t, 3H)' IR (KBr) 3460, 3355, 1615, 1602, 1580 cm$^1$.

Then, to a suspension of the monoazo amine (1.70 g, 5 mmol) in 5N HCl (3.5 ml) and water (9 ml) was added 2M sodium nitrite (2.75 ml, 5.5 mmol) in 3 portions over 3 min at room temperature. The mixture was mixed 5 min at room temperature and cooled to 0°–5° C. In a second beaker, phenol (0.56 g, 6 mmol), sodium acetate (1.6 g, 20 mmol), and acetic acid (12 ml) were mixed and cooled to 0.5° C. The diazonium solution was added to the acetic acid solution all at once at 0°–5° C. The mixture was stirred 30 min and basified with saturated sodium carbonate to pH=7.0. The solid was filtered and washed with warm water. The solid was worked with ethanol (30 ml) and acetone (5 ml) on a steam bath and filtered to remove insoluble material. The solvent was removed and the residual material dissolved in toluene and chromatographed on silica gel (hexane-ethyl acetate, 5:1). Cuts 6–8 gave pure bisazohexyloxyphenol (0.80 g, 36%): mp 151° C.; $^1$H NMR (CDCl$_3$) delta=7.80(m, 4H), 7.48 and 7.30(2s, 2H), 6.85(m, 4H), 6.22(bs, 1H), 3.96(s and t, 5H), 2.63(s, 3H), 1.9–1.2(m, 8H), 0.9(t, 3H); IR (KBr) 3600–3200, 1600, 1580 cm$^{-1}$.

EXAMPLE 11

This example illustrates the preparation of a bisazohexyloxyperimidine, a red dye.

was prepared as follows. To a suspension of 4-hexyloxyaniline (5.8 g, 30 mmol) in 10N hydrochloric acid (10 ml) and water (30 ml) was added 2M sodium nitrite solution (16 ml, 32 mmol) over 5 minutes at 0°–5° C. The solution was stirred occasionally over 30 minutes at 0°–5° C. In a second beaker 3-methyl aniline (4.27 g, 40 mmol), sodium acetate (8.4 g, 0.1 mol) and acetic acid (50 ml) were mixed well for 5 minutes and cooled to 0°–5° C. The diazonium solution was added to the acetic acid solution all at once and the mixture stirred over 30 minutes at 0°–5° C. The mixture was basified with 25% sodium hydroxide to a pH of 10, filtered, and the solid was washed with hot water. The solid was dried under vacuum and recrystallized from ethanol to give monoazo amine (2.35 g, 19%). The monoazo amine (0.62 g, mmol was mixed with 5N HCl (1.4 ml) and diluted with water (3.6 ml) in a 25 ml beaker. A solution of 2M sodium nitrite (1.1 ml, 2.2 mmol) was added over 3 minutes; the mixture was stirred 2 minutes; and cooled to 0° C. The mixture was stirred occasionally over 10 minutes at 0° C. In a second 50 ml beaker, a mixture of 2,3-dihydro-1,3-dimethyl-2-octyl perimidine (prepared in Example 4) (0.68 g, 2.2 mmol), sodium acetate (0.5 g) and nitric acid (8 ml) were mixed and cooled to 0° C. The diazonium solution was poured into the acetic acid solution all at once. The mixture was kept at 0°–5° C. for 1 hour and, then, basified with saturated potassium carbonate solution. The crude gummy solid was purified on silica with hexane-THF (6:1) and recrystallized from THF-ethanol (5:1, 12 ml) to give the diazo perimidine red dye (0.12 g, 9.5%): mp 90° C.; and lambda max (CHCl₃)=553 nm, e=28,077. This dye was measured to have a solubility in CS1018 of 1.6 wt %.

Coupling of 2,3-dihydro-1,3-dimethyl-2-octyl perimidine (Example 7) with the diazonium ion used in Example 11 gave a crude solid. The solid was purified by column chromatography (silica; hexane-THF, 3:1) and recrystallized from THF-ethanol (2:1) to give the diazo perimidine dye having the structure shown in Table 3 (0.06 g): mp 192° C. This dye was measured to have a solubility of less than 0.2 wt % in CS 1018.

EXAMPLE 12

A black liquid crystal guest-host formulation was prepared by adding each dye component into a 2 ml "Wheaton" vial, adding the liquid crystal host, and then stirring at 80° C. on a heating block for 24 hours. The liquid crystal host and guest dyes were present in the following amounts.

| Compound | Color | Parts (by weight) |
| --- | --- | --- |
| ZLI 3654 (host) | — | 1125 |
| Bisazohexyloxynaphthyl perimidine (Example 8) | Blue | 30 |
| Bisazohexyloxyperimidine perimidine (Example 11) | Red | 15 |
| Bisazohexyloxyphenol (Example 10) | Yellow | 15 |

This neutral black mixture was subsequently used to fill a liquid crystal display cell having a 5 micrometer spacing by capillary action. This was performed at elevated temperatures (100° C.) to reduce the viscosity of the formulation. An electric potential of 30 volts (square wave) was applied across this display cell and it exhibited a contrast ratio of 7.5 when measured with one polarizer. In addition to the direct driving scheme for switching the light absorption properties of a pixel area, multiplexed driving schemes were also employed. One such approach yielded a contrast ratio of 2.7.

EXAMPLE 13

A black guest-host formulation was prepared as in Example 12, using the following.

| Compound | Color | Parts (by weight) |
| --- | --- | --- |
| SCE 10 (host) | — | 1152 |
| Diazohexyloxynaphthyl perimidine (Example 8) | Blue | 24 |
| Diacohexyloxyperimidine perimidine (Example 11) | Red | 19 |
| Biszaohexyloxyphenol (Example 10) | Yellow | 15 |

Results similar to those described in Example 12 were obtained using this host. A contrast ratio of 11.2 was observed using a 30 volt square wave applied across a 5 micrometer cell. In addition to an improved contrast ratio, the selection of a different host affords the opportunity of different use temperatures for a particular device.

While the invention has been described with respect to specific embodiments, it should be understood that they are not intended to be limiting and that many variations and modifications are possible without departing from the scope of this invention.

What is claimed is:

1. An arylazo or poly(arylazo) dichroic dye having (a) one to five arylazo groups wherein the aryl radicals are selected from the group consisting of napththyl, anthracyl and phenyl radicals, and at least one aryl radical is a naphthylor anthracyl radical, and (b) having at least one 2,3-dihydro-1,3-dialkyl perimidine substituent.

2. A dichroic dye as claimed in claim 1 having the formula:

wherein A is selected form the group consisting of a naphthyl radical (I), anthracyl radical (II) or anthracyl radical (III) and X is selected form the group consisting of a naphthyl radical (I), anthracyl radical (II), anthracyl radical (III) and phenyl radical

(IV):

$R^1$ and $R^2$ are selected form the group consisting of —$NO_2$, —CN, Br, Cl, F, —$CO_2R^3$, —$NR^4R^5$, —$OR^6$ or $R^6$; $R^3$, $R^4$, $R^5$ and $R^6$ are selected from the group consisting of H or $C_1$ to $C_{10}$ alkyl groups; n and m are integers of 0 through 4; when n=0, Z is selected from the group consisting of —$NO_2$, —CN, —$CO_2R^3$, F, Cl, Br, $R^6$, —$OR^6$, $CH_3SO_2$—, $CF_3SO_2$—, $C_6H_5SO_2$—, —$CF_3$, —$C(O)CF_3$, 2,2-dicyanovinyl and 1,2,2-tricyanovinyl, and wherein $R^7$ is selected from the group consisting of H and $C_1$ to $C_{10}$ alkyl groups; $R^8$ and $R^9$ are selected from the group consisting of H and $C_1$ to $C_{20}$ alkyl groups or form a $C_4$ to $C_8$ cycloaliphatic ring; when n is an integer of from 1 through 4, Z is as defined for Z when n=O or —$NR^4R^5$; and B is wherein $R^{10}$ is selected from the group consisting of $C_1$ to $C_{10}$ alkyl groups; $R^{11}$ and $R^{12}$ are selected from the group consisting of H and $C_1$ to $C_{20}$ alkyl groups or form a $C_4$ to $C_8$ cycloaliphatic ring.

3. A dichroic dye as claimed in claim 1 which is a monoazo dye.

4. A dichroic dye as claimed in claim 1 which is a bisazo dye.

5. A dichroic dye as claimed in claim 2 which is a monoazo dye.

6. A dichroic dye as claimed in claim 2 which is a bisazo dye.

7. A dichroic dye as claimed in claim 2 where $R^{11}$ and $R^{12}$ are selected form the group consisting of H and $C_1$ and $C_{20}$ alkyl groups.

8. A dichroic dye as claimed in claim 2 where n=0 and m=0, n=1 and m=0, or n=1 and m=1; A has the formula (I); and X has the formula (IV).

9. A dichroic dye as claimed in claim 8 wherein n=1, m=0 or 1.

10. A dichroic dye as claimed in claim 9 wherein Z is selected from the group consisting of —$NO_2$, —CN, —$CO_2R^3$, $CH_3SO_2$, $CF_3SO_2$—, —$CF_3$, —$C(O)CF_3$, 2,2-dicyanovinyl, 1,2,2-tricyanovinyl and —$NR^4R^5$.

11. A dichroic dye as claimed in claim 1 which is a trisazo dye.

12. A dichroic dye as claimed in claim 2 which is a trisazo dye.

13. A dichroic dye as claimed in claim 1 which is a tetraazo dye.

14. A dichroic dye as claimed in claim 2 which is a tetraazo dye.

15. A dichroic dye as claimed in claim 1 which is a pentaazo dye.

16. A dichroic dye as claimed in claim 2 which is a pentaazo dye.

17. A dichroic dye as claimed in claim 6 where $R^{11}$ and $R^{12}$ are selected from the group of H and $C_1$ to $C_{20}$ alkyl groups.

* * * * *

UNITED STATES PATENT AND TRADEMARK OFFICE
CERTIFICATE OF CORRECTION

PATENT NO. : 5,326,865
DATED : July 5, 1994
INVENTOR(S) : Robert P. Grasso, Michael K. O'Brien and Paul J. Shannon It is certified that error appears in the above-identified patent and that said Letters Patent is hereby corrected as shown below:

In col. 18, claim 1 (a) line 53 in place of the word "naphthylor", should read --naphthyl or--.

In col. 18, claim 2 (line 63) in place of the words "A is selected form the group", should read --A is selected from the group--.

In col. 18, claim 2 line 65 in place of the words "X is selected form the group", should read --X is selected from the group--.

In col. 19, claim 2 line 45 in place of the word "form", should read --from--.

In col. 20, claim 7 line 23 in place of the words "$R^{12}$ are selected form the group", should read --$R^{12}$ are selected from the group--.

Signed and Sealed this

Twenty-sixth Day of September, 1995

Attest:

BRUCE LEHMAN

*Attesting Officer*        *Commissioner of Patents and Trademarks*